US012650396B2

(12) United States Patent
Mizutani et al.

(10) Patent No.: US 12,650,396 B2
(45) Date of Patent: Jun. 9, 2026

(54) GAS MEASURING DEVICE

(71) Applicants:SINTOKOGIO, LTD., Nagoya (JP);
**National University Corporation
TOYOHASHI UNIVERSITY OF
TECHNOLOGY**, Toyohashi (JP)

(72) Inventors: Manase Mizutani, Nagoya (JP);
Yoshihisa Suzuki, Nagoya (JP);
Toshihiko Noda, Toyohashi (JP);
Kazuaki Sawada, Toyohashi (JP)

(73) Assignees: SINTOKOGIO, LTD., Nagoya (JP);
**National University Corporation
TOYOHASHI UNIVERSITY OF
TECHNOLOGY**, Toyohashi (JP)

( * ) Notice: Subject to any disclaimer, the term of this
patent is extended or adjusted under 35
U.S.C. 154(b) by 522 days.

(21) Appl. No.: 18/129,279

(22) Filed: Mar. 31, 2023

(65) Prior Publication Data

US 2023/0314354 A1     Oct. 5, 2023

(30) Foreign Application Priority Data

Apr. 5, 2022     (JP) ................................. 2022-062887

(51) Int. Cl.
*G01N 25/22*        (2006.01)
*G01N 33/00*        (2006.01)
(52) U.S. Cl.
CPC ......... *G01N 25/22* (2013.01); *G01N 33/0027*
(2013.01)
(58) Field of Classification Search
CPC .................................................... G01N 25/22
See application file for complete search history.

(56) References Cited

U.S. PATENT DOCUMENTS

| | | | | |
|---|---|---|---|---|
| 5,465,607 | A | * 11/1995 | Corrigan | ............... G01N 1/2214 |
| | | | | 250/282 |
| 6,110,860 | A | * 8/2000 | Inoue | .................... B01D 53/945 |
| | | | | 502/223 |
| 2004/0020176 | A1* | 2/2004 | Kong | .................... F01N 3/0857 |
| | | | | 55/282.3 |
| 2017/0363556 | A1 | 12/2017 | Nagase et al. | |
| 2019/0212288 | A1* | 7/2019 | Swanson | ................ G01N 31/12 |

(Continued)

FOREIGN PATENT DOCUMENTS

| | | |
|---|---|---|
| DE | 19916798 A1 | 11/2000 |
| DE | 10245947 A1 | 4/2004 |
| JP | 2000-055852 A | 2/2000 |

(Continued)

OTHER PUBLICATIONS

Extended European Search Report issued Jul. 5, 2023 in Application No. 23164952.6.

(Continued)

*Primary Examiner* — John E Breene
*Assistant Examiner* — Alex T Devito
(74) *Attorney, Agent, or Firm* — Faegre Drinker Biddle &
Reath LLP

(57)     ABSTRACT

A gas measuring device includes: a filter to which a power supply that applies a voltage or current is connected, which generates resistance heat, and which combusts a predetermined combustible gas in contact therewith; and a gas sensor configured to detect the combustible gas that has passed through the filter.

4 Claims, 3 Drawing Sheets

(56) References Cited

U.S. PATENT DOCUMENTS

| | | | |
|---|---|---|---|
| 2020/0025701 | A1 | 1/2020 | Brown et al. |
| 2023/0079310 | A1 | 3/2023 | Suzuki et al. |

FOREIGN PATENT DOCUMENTS

| | | |
|---|---|---|
| JP | 2015-127642 A | 7/2015 |
| JP | 2017-223557 A | 12/2017 |
| JP | 2020-523182 A | 8/2020 |
| WO | WO-2018/231551 A1 | 12/2018 |
| WO | 2019/188692 A1 | 10/2019 |
| WO | WO-2021/176933 A1 | 9/2021 |

OTHER PUBLICATIONS

Japanese Office Action issued Oct. 7, 2025, in Application No. 2022-062887.

European Communication pursuant to Article 94(3) EPC issued Aug. 6, 2025 in Application No. 23164952.6.

* cited by examiner

GAS MEASURING DEVICE

CROSS-REFERENCE TO RELATED APPLICATION

This application is based on Japanese Patent Application No. 2022-062887 filed with Japan Patent Office on Apr. 5, 2022, the entire contents of which are hereby incorporated by reference.

TECHNICAL FIELD

The present disclosure relates to a gas measuring device.

BACKGROUND

Published Japanese Translation No. 2020-523182 of the PCT International Publication discloses a combustible gas sensor including a filter containing a metal salt and a sensing element. This combustible gas sensor removes a gas including a corrosive sulfur compound by reacting it with the metal salt contained in the filter.

SUMMARY

Incidentally, gases to be measured may include a plurality of types of gases. In such a case, it is impossible to distinguish which gas is being detected, and thus screening of gases to be detected is required. The combustible gas sensor described in Published Japanese Translation No. 2020-523182 of the PCT International Publication screens the gases to be detected by chemical reaction of the filter, but can screen only a specific gas that reacts with a metal salt. The present disclosure provides a gas measuring device that can properly screen a combustible gas.

A gas measuring device according to an aspect of the present disclosure includes: a filter; and a gas sensor configured to detect a gas that has passed through the filter. A power supply that applies a voltage or current is connected to the filter. The filter generates resistance heat and combusts a combustible gas in contact therewith.

When a voltage or current is applied to the gas measuring device, the filter generates resistance heat and raises its temperature. When the temperature of the filter rises to the ignition point of the combustible gas, the combustible gas in contact with the filter is combusted. The combusted combustible gas is not sensed by the gas sensor. At this time, since the ignition point differs depending on the type of combustible gas, the gas measuring device can screen the combustible gas sensed by the gas sensor by changing the temperature of the filter.

In an embodiment, the gas measuring device may further include a signal generation unit, a control unit, an acquisition unit, and an output unit. The signal generation unit outputs a synchronization signal for determining a timing. On the basis of the control signal for determining the temperature of the filter and the synchronization signal, the control unit controls the power supply such that the temperature of the filter becomes a temperature determined with the control signal at the timing determined with the synchronization signal. The acquisition unit acquires a detection value of the gas sensor at the timing determined with the synchronization signal. The output unit outputs the detection value and the control signal in association with each other. In this case, the gas measuring device can output the detection value and the synchronization signal in association with each other.

In an embodiment, the gas measuring device may further include a determination unit configured to determine a gas type on the basis of a pre-acquired relationship, the detection value, and the control signal. The pre-acquired relationship is a relationship among the gas type, the detection value, and the control signal. In this case, the gas measuring device can determine the gas type of the combustible gas.

In an embodiment, the filter may be made of at least one of tungsten, a nickel-chromium alloy, molybdenum, and copper.

According to the gas measuring device of the present disclosure, it is possible to properly screen a combustible gas.

DETAILED DESCRIPTION

Embodiments of the present disclosure will be described below with reference to the drawings. In the following description, the same or corresponding elements are denoted by the same reference signs, and redundant description will not be repeated. The dimensional proportions of the drawings do not necessarily match those of the description. The terms "upper," "lower," "left," and "right" are based on the illustration and are for convenience.

[Configuration of Gas Measuring Device]

Figure 1:
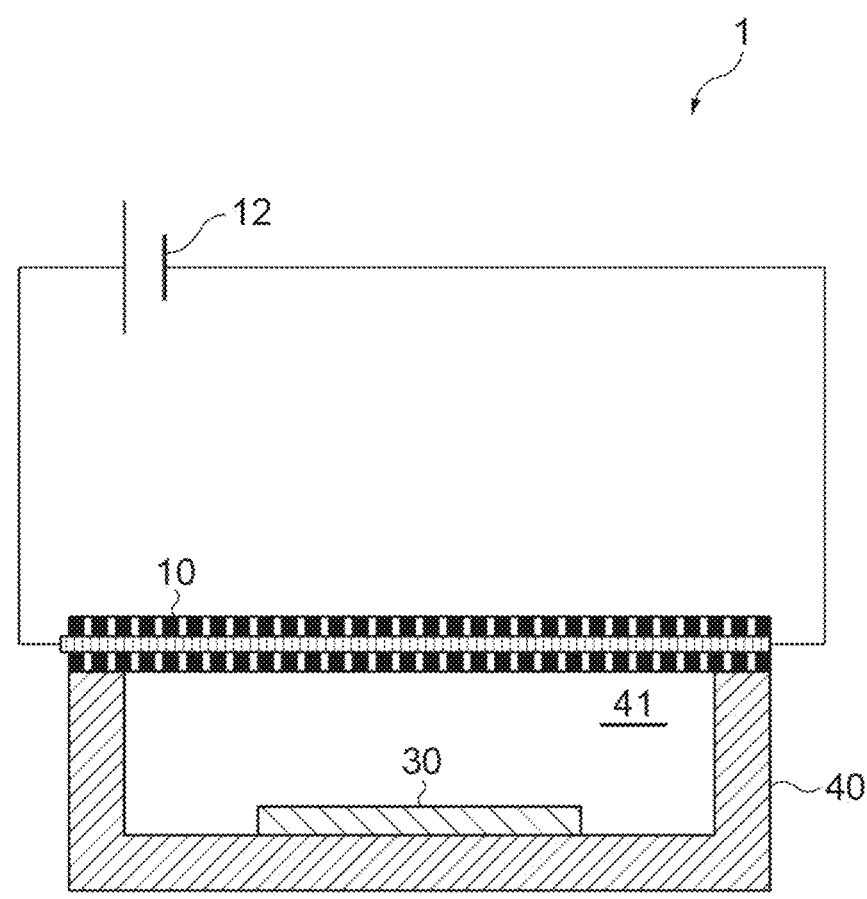
FIG. 1 is a cross-sectional view showing an example of a gas measuring device according to an embodiment.

FIG. 1 is a cross-sectional view showing an example of a gas measuring device according to an embodiment. The gas measuring device 1 shown in FIG. 1 is a device for measuring gas components. The gas measuring device 1 may be provided as an electric circuit part. As an example, the gas measuring device 1 is a micro electro mechanical systems (MEMS) device. The gas measuring device 1 includes a filter 10, a gas sensor 30, and a base member 40.

The base member 40 defines a space therein. The base member 40 is formed of a gas impermeable material. An upper portion of the base member 40 is open, and the base member 40 has an opening that communicates with the space. The filter 10 is disposed to block the opening in the upper portion of the base member 40. The filter 10 is a substantially plate-shaped member and is formed of a gas permeable material. The filter 10 and the base member 40 are joined together such that there is no gap through which a gas permeates. Accordingly, the filter 10 and the base member 40 define a gas chamber 41.

The filter 10 is an electrical conductor and generates heat when energized. The filter 10 is made of a metal with high resistance such as tungsten (W), a nickel-chromium alloy, or molybdenum (Mo). The filter 10 may be made of copper (Cu). The filter 10 is connected to a power supply 12 that applies a voltage or current and generates heat due to the application of a voltage or current. The filter 10 includes a plurality of gaps ranging from micro-order to nano-order.

The gas passes through the gaps of the filter 10. The heated filter 10 combusts a combustible gas included in the gas.

The gas sensor 30 is provided inside the gas chamber 41. As an example, the gas sensor 30 is provided downstream of the filter 10. The gas sensor 30 is provided on a side where the gas has passed through the filter 10 after coining into contact with the filter 10. The gas sensor 30 detects a screened gas that has passed through the filter 10 but has not been combusted. The gas sensor 30 is, for example, a gas sensor using a semiconductor. The gas sensor 30 has a sensing surface for detecting a gas. In this case, the gas sensor 30 outputs gas molecules in contact with the sensing surface of the gas sensor 30 as a detection value.

[Control Circuit of Gas Measuring Device]

Figure 2A:
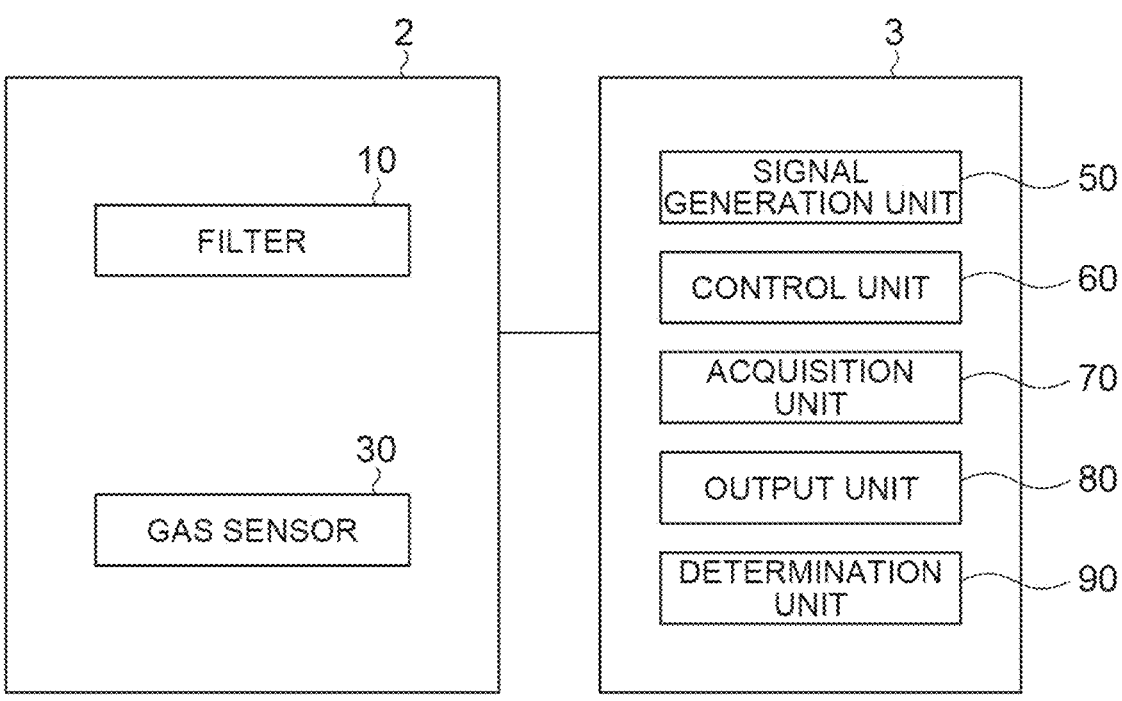
FIG. 2A is a block diagram showing an example of the gas measuring device according to the embodiment.

FIG. 2A is a block diagram showing an example of the gas measuring device 1 according to the embodiment. The gas measuring device 1 includes a measuring unit 2 and a circuit unit 3. The measuring unit 2 is an example of a gas measuring device. The circuit unit 3 includes a signal generation unit 50, a control unit 60, an acquisition unit 70, an output unit 80, and a determination unit 90. The circuit unit 3 may be constituted by an electric circuit, for example. The circuit unit 3 may be constituted by a general purpose computer that includes, for example, an arithmetic device such as a central processing unit (CPU), a storage device such as a read only memory (ROM), a random access memory (RAM), a hard disk drive (HDD), a communication device, and the like.

Figure 2B:
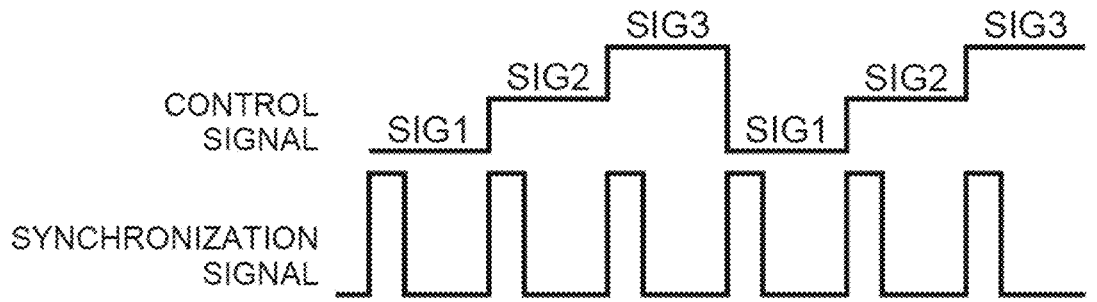
FIG. 2B shows examples of a control signal and a synchronization signal.

As an example, the signal generation unit 50 outputs a control signal and a synchronization signal to the control unit 60 and the acquisition unit 70. The control signal is a signal for determining a temperature of the filter 10. The synchronization signal is a signal for determining a timing for the control unit 60 and the acquisition unit 70. The control unit 60 controls the power supply 12 on the basis of the control signal and the synchronization signal such that the voltage or current for controlling the temperature of the filter 10 is applied to the filter 10. FIG. 2B shows examples of the control signal and the synchronization signal. In FIG. 2B, the control signal includes three types of signals SIG1, SIG2, and SIG3. SIG1, SIG2, and SIG3 are control signals corresponding to three types of temperatures. The synchronization signal is a rectangular wave based on an oscillator such as a crystal oscillator. The control unit 60 controls the temperature of the filter 10 to a temperature corresponding to the control signal. The acquisition unit 70 acquires the detection value on the basis of the synchronization signal.

The control unit 60 may output a waveform corresponding to the temperature of the filter 10 upon receiving the rectangular wave of the synchronization signal a predetermined number of times. As an example, with the control signal that changes in three steps in FIG. 2B, the control unit 60 controls the temperature of the filter 10 in three steps. The temperature of the filter 10 may be controlled steplessly. In this case, the control signal exhibits a triangular wave or a sine wave.

The acquisition unit 70 acquires the detection value output by the gas sensor 30 upon receiving the rectangular wave of the synchronization signal a predetermined number of times. Therefore, the acquisition unit 70 can acquire the detection value corresponding to a change in the temperature of the filter 10 due to the control signal. The predetermined number of times of reception of the rectangular wave when the acquisition unit 70 acquires the detection value may be equal to or greater than the number of times of reception of the rectangular wave when the control unit 60 performs output. By setting the time at which the acquisition unit 70 acquires the detection value to be later than the time at which the control unit 60 performs output, it is possible for the acquisition unit 70 to acquire the detection value at a timing when the amount of the gas in contact with the filter 10 reaches a maximum after the temperature of the filter 10 changes.

The output unit 80 outputs the control signal and the detection value acquired by the acquisition unit 70 in association with each other. The determination unit 90 determines the gas on the basis of a pre-acquired relationship among the gas, the detection value, and the control signal, and the detection value and the control signal output from the output unit 80. Combinations of the gas, the detection value, and the control signal are acquired in advance and are stored, for example, as a gas characteristic table. The determination unit 90 refers to the gas characteristic table on the basis of the combination output from the output unit 80 and determines the gas.

[Operation of Gas Measuring Device]

Figure 3A:
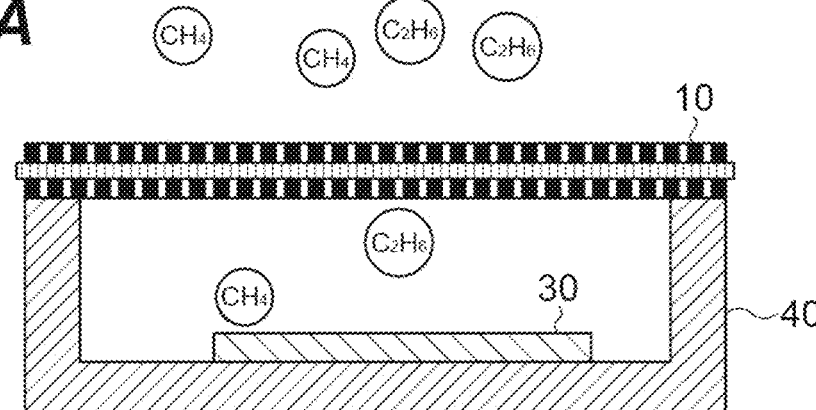
FIG. 3A is a schematic view illustrating reactions of gas molecules according to a temperature of a filter.
Figure 3B:
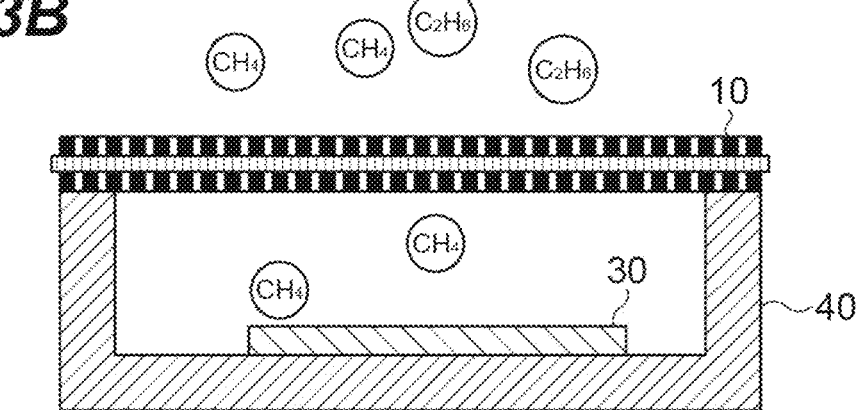
FIG. 3B is another schematic view illustrating reactions of gas molecules according to a temperature of a filter.
Figure 3C:
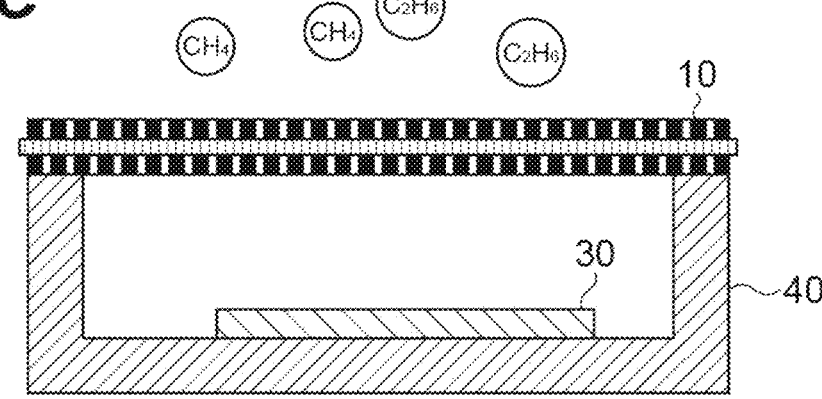
FIG. 3C is yet another schematic view illustrating reactions of gas molecules according to a temperature of a filter.

FIGS. 3A to 3C are schematic views illustrating behaviors of the gas molecules according to the temperature of the filter 10. As an example, the combustible gas that is a detection target is a mixed gas including hydrocarbons such as methane ($CH_4$) and ethane ($C_2H_6$). The gas measuring device 1 has the gas sensor 30 capable of detecting specific types of molecules among hydrocarbons such as methane ($CH_4$) and ethane ($C_2H_6$). In the present embodiment, as an example, the gas measuring device 1 detects methane ($CH_4$) and ethane ($C_2H_6$).

As shown in FIG. 2B, first, the temperature of the filter 10 is changed by the control unit 60 which operates on the basis of the control signal and the synchronization signal. FIG. 3A shows the behavior of the gas molecules in contact with the filter 10 in a case where the control signal is SIG1. As an example, in a case where the control signal is SIG1, the control unit 60 controls the power supply 12 such that no voltage or current is applied to the filter 10. Therefore, the filter 10 does not generate heat. In a case where the control signal is SIG1, methane ($CH_4$) and ethane ($C_2H_6$) are not combusted. The gas sensor 30 detects methane ($CH_4$) and ethane ($C_2H_6$).

FIG. 3B shows the behavior of the gas molecules in contact with the filter 10 in a case where the control signal is SIG2. In a case where the control signal is SIG2, the control unit 60 controls the power supply 12 such that a voltage or current is applied to the filter 10. The filter 10 generates heat up to the ignition point of ethane ($C_2H_6$) when energized. The ignition point of ethane ($C_2H_6$) is 520° C., for example. Ethane ($C_2H_6$) passing through the filter 10 is combusted. Methane ($CH_4$) is not combusted because it has a higher ignition point than ethane ($C_2H_6$). The gas sensor 30 detects methane ($CH_4$).

FIG. 3C shows the behavior of the gas molecules in contact with the filter 10 in a case where the control signal is SIG3. In a case where the control signal is SIG3, the control unit 60 controls the power supply 12 such that a larger voltage or current is applied to the filter 10 than in a case where the control signal is SIG2. The filter 10 generates heat up to the ignition point of methane ($CH_4$) when energized. The ignition point of methane ($CH_4$) is 537° C., for example. Methane ($CH_4$) and ethane ($C_2H_6$) passing through the filter 10 are combusted. The gas sensor 30 does not detect methane ($CH_4$) and ethane ($C_2H_6$). The gas sensor 30 detects the absence of methane ($CH_4$) and ethane ($C_2H_6$).

Next, the acquisition unit 70 acquires the detection value output by the gas sensor 30 on the basis of the synchronization signal. The output unit 80 outputs the control signal and the detection value acquired by the acquisition unit 70 in association with each other. The determination unit 90 determines the gas on the basis of the gas characteristic table, the detection value acquired by the acquisition unit 70, and the control signal. On the basis of the pre-acquired relationship the previously obtained relationship between the temperature of the filter 10 indicated by the control signal and the detection value, it is determined that the mixed gas includes methane ($CH_4$) and ethane ($C_2H_6$).

[Outline of Embodiment]

In the gas measuring device 1, when a voltage or current is applied thereto, the filter 10 generates resistance heat and raises its temperature. When the temperature of the filter 10 rises to the ignition point of the combustible gas, the combustible gas in contact with the filter 10 is combusted. The combusted combustible gas is not sensed by the gas sensor 30. At this time, since the ignition point differs depending on the type of combustible gas, the gas measuring device can screen the combustible gas by changing the temperature of the filter 10.

In the gas measuring device 1, on the basis of the control signal for determining the temperature of the filter 10 and the synchronization signal, the control unit 60 controls the power supply 12 such that the temperature of the filter 10 becomes a temperature determined with the control signal at the timing determined with the synchronization signal. Then, the acquisition unit 70 acquires the detection value of the gas sensor 30 at the timing determined with the synchronization signal. In this way, the gas measuring device 1 can output the detection value and the synchronization signal in association with each other.

In the gas measuring device 1, the determination unit 90 determines the gas type on the basis of the pre-acquired relationship, and the detection value and the control signal. As a result, the gas measuring device 1 can determine the gas type of the combustible gas.

Modification Example

In the above, various exemplary embodiments have been described, but the present disclosure is not limited to the above exemplary embodiments, and various omissions, substitutions, and modifications may be made.

The filter 10 and the gas sensor 30 may be manufactured by being combined after they are separately formed. The filter 10 and the gas sensor 30 may be manufactured as a single body.

The filter 10 may define a space therein. In this case, the filter 10 may be made of a material that is flexible and conductive and has a small amount of thermal deformation. The filter 10 is made of, for example, a metal mesh. A lower portion of the filter 10 is open, and the filter 10 has an opening that communicates with the space. The plate-shaped base member 40 is disposed to block the opening in the lower portion of the filter 10. Accordingly, the filter 10 and the base member 40 may define the gas chamber 41. In this case, the gas sensor 30 may be spaced apart from the base member 40 and disposed in the center of the gas chamber 41.

The signal generation unit 50 may be integrated with the control unit 60. The acquisition unit 70 may be integrated with the output unit 80. The output unit 80 may be integrated with the determination unit 90.

The gas measuring device 1 may be configured not to include the base member 40 and the gas chamber 41. In this case, the gas measuring device 1 is configured such that the filter 10 is in close contact with the gas sensor 30. The gas measuring device 1 may include M types of gas sensors (M is an integer equal to or greater than 2). In a case where M is 3 or more, the M types of gas sensors may include the same type of sensors. Further, the temperature of the filter 10 may be controlled in N steps (N is an integer equal to or greater than 2). In this case, the gas measuring device 1 can measure a maximum of M×N combinations of gas types.

The gas measuring device 1 may be configured not to include the determination unit 90. In this case, in the gas measuring device 1, the output unit 80 outputs the measured value and the control signal to the outside.

What is claimed is:

1. A gas measuring device comprising:
a filter connected to a power supply that applies a voltage or current, configured to generate resistance heat, and configured to combust a predetermined combustible gas in contact therewith;
a gas sensor configured to detect the combustible gas that has passed through the filter;
a signal generation unit configured to output a synchronization signal for determining a timing;
a control unit configured to control the power supply on the basis of a control signal for determining a temperature of the filter and the synchronization signal such that the temperature of the filter becomes a temperature determined with the control signal at the timing determined with the synchronization signal;
an acquisition unit configured to acquire a detection value of the gas sensor at the timing determined with the synchronization signal; and
an output unit configured to output the detection value and the control signal in association with each other.

2. The gas measuring device according to claim 1, further comprising a determination unit configured to determine a gas type on the basis of a pre-acquired relationship, the detection value, and the control signal,
wherein the pre-acquired relationship is a relationship among the gas type, the detection value, and the control signal.

3. The gas measuring device according to claim 2, wherein the filter is made of at least one of tungsten, a nickel-chromium alloy, molybdenum, and copper.

4. The gas measuring device according to claim 1, wherein the filter is made of at least one of tungsten, a nickel-chromium alloy, molybdenum, and copper.

* * * * *